(12) United States Patent
Spector et al.

(10) Patent No.: US 11,974,854 B2
(45) Date of Patent: May 7, 2024

(54) ALGORITHMIC TECHNIQUES FOR DEDUCTION OF FUNCTIONAL CHARACTERISTICS OF CARDIAC TISSUE IN CARDIAC ELECTRICAL FIBRILLATION FROM A DENSELY PACKED ARRAY OF HIGH-RESOLUTION ELECTRODES

(71) Applicant: CoreMap, Inc., Colchester, VT (US)

(72) Inventors: Peter S. Spector, Colchester, VT (US); Sarah Kalil, Stowe, VT (US); Daniel Klebanov, Arlington, MA (US)

(73) Assignee: CoreMap, Inc., Colchester, VT (US)

( * ) Notice: Subject to any disclaimer, the term of this patent is extended or adjusted under 35 U.S.C. 154(b) by 0 days.

(21) Appl. No.: 17/379,393

(22) Filed: Jul. 19, 2021

(65) Prior Publication Data

US 2022/0015682 A1    Jan. 20, 2022

Related U.S. Application Data

(60) Provisional application No. 63/054,014, filed on Jul. 20, 2020.

(51) Int. Cl.
*A61B 5/361* (2021.01)
*A61B 5/287* (2021.01)
*A61B 5/367* (2021.01)

(52) U.S. Cl.
CPC .............. *A61B 5/361* (2021.01); *A61B 5/287* (2021.01); *A61B 5/367* (2021.01); *A61B 2562/046* (2013.01)

(58) Field of Classification Search
CPC ...................................................... A61B 5/361

USPC ......................................................... 600/512
See application file for complete search history.

(56) References Cited

U.S. PATENT DOCUMENTS

| | | |
|---|---|---|
| 5,687,737 A | 11/1997 | Branham et al. |
| 5,846,196 A | 12/1998 | Siekmeyer et al. |
| 6,522,905 B2 | 2/2003 | Desai |
| 8,391,947 B2 | 3/2013 | Urman et al. |
| 10,244,960 B2 | 4/2019 | Kordis et al. |
| 11,039,773 B2 | 6/2021 | Sterrett et al. |
| 11,089,927 B1 | 8/2021 | Neill |
| 2007/0197892 A1 | 8/2007 | Shen et al. |
| 2011/0137369 A1 | 6/2011 | Ryu et al. |
| 2013/0324871 A1 | 12/2013 | Dubois et al. |
| 2014/0148872 A1 | 5/2014 | Goldwasser et al. |
| 2014/0200429 A1 | 7/2014 | Spector et al. |
| 2017/0042449 A1 | 2/2017 | Deno et al. |
| 2017/0065198 A1 | 3/2017 | Ruppersberg |
| 2017/0079542 A1* | 3/2017 | Spector ............... A61B 5/35 |
| 2017/0281031 A1 | 10/2017 | Houben et al. |

(Continued)

OTHER PUBLICATIONS

Calkins et al., 2009, Treatment of Atrial Fibrillation with Antiarrhythmic Drugs or Radiofrequency Ablation, Two Systematic Literature Reviews and Meta-Analyses, Circ. Arrhythmia Electrophysiol., 2(4):349-61.

(Continued)

*Primary Examiner* — Nicole F Lavert
(74) *Attorney, Agent, or Firm* — Withers Bergman LLP; Thomas C. Meyers

(57) ABSTRACT

The present disclosure describes cardiac mapping techniques that find particular use in assessing fibrillation, and which also improve the ability to correctly identify local activation time from signals in any rhythm.

22 Claims, 18 Drawing Sheets

(56) References Cited

U.S. PATENT DOCUMENTS

| | | | |
|---|---|---|---|
| 2018/0325400 A1* | 11/2018 | Dubois | A61B 18/1492 |
| 2019/0150842 A1 | 5/2019 | Shuros et al. | |
| 2019/0201687 A1 | 7/2019 | Ahmed | |
| 2020/0138319 A1 | 5/2020 | Spector | |
| 2020/0146578 A1 | 5/2020 | Dang et al. | |
| 2021/0059745 A1 | 3/2021 | Highsmith | |
| 2021/0077183 A1 | 3/2021 | Basu et al. | |

OTHER PUBLICATIONS

Spector et al., 2009, Meta-analysis of Ablation of Atrial Flutter and Supraventricular Tachycardia, Am. J. Cardiol., 104 (5): 671-677.

International Search Report and Written Opinion issued in International Application No. PCT/US2021/042192, dated Nov. 4, 2021, 7 pages.

International Search Report and Written Opinion issued in International Application No. PCT/US2021/055984, dated Feb. 1, 2022, 7 pages.

International Search Report and Written Opinion issued in International Application No. PCT/US2022/030637, dated Aug. 17, 2022, 10 pages.

International Search Report and Written Opinion issued in International Application No. PCT/US2022/053670, dated Apr. 4, 2023, 7 pages.

* cited by examiner

ALGORITHMIC TECHNIQUES FOR DEDUCTION OF FUNCTIONAL CHARACTERISTICS OF CARDIAC TISSUE IN CARDIAC ELECTRICAL FIBRILLATION FROM A DENSELY PACKED ARRAY OF HIGH-RESOLUTION ELECTRODES

FIELD OF INVENTION

This disclosure applies to electro-anatomical mapping. Such mapping can map persistent atrial fibrillation for the purposes of guidance for ablation therapy.

BACKGROUND

Electro-anatomical mapping of the heart is a technique commonly used in cardiac electrophysiology to plan, optimize, and verify ablation therapy for a wide variety of cardiac arrhythmias. In typical use, an intra-cardiac mapping catheter with one or more electrodes collects electrical data from the endocardial (or epicardial) surface to determine local activation timing for multiple locations on the surface of the heart chamber. By taking advantage of similarity between beats, data from multiple beats may be combined to form a map of activation across an entire chamber, thereby revealing candidate ablation target sites, which have the highest likelihood of terminating and preventing arrhythmia while sparing healthy cardiac tissue.

However, unlike periodic arrhythmias, such as flutter, fibrillation is not amenable to the same type of multi-beat activation mapping described above, as there is no timing reference common to all beats, which is required for stitching together "beats". Furthermore, due to the complexity of electrical differences between heart cells that occur over smaller distances, it is common to obtain complex fractionated signals.

Current technologies cannot effectively ascertain patient-specific maps of fibrillation. Thus, treatments are limited to "one size fits all approaches". Unfortunately, antiarrhythmic medications are only effective in approximately half of the 33 million patients suffering from, for example, atrial fibrillation (AF). Accurate activation mapping is further complicated by the complexity of projecting sequentially acquired local activation time measurements from a region in 3D space, onto a stationary representation of the heart's surface. Challenges due to this projection can result in erroneous interpretation of conduction direction.

Catheter ablation has emerged as the treatment of choice for patients experiencing drug-resistant AF. (Calkins et al., 2(4) Circ. *Arrhythmia Electrophysiol.*, 349-61 (2009)). Unfortunately, current ablation methods for AF fail for approximately 30% of patients. Id. at 354. Despite the difficulties in AF patients, ablation when used in patients with other heart arrhythmias achieves a 95% success rate. (Spector et al., 104(5) *Am. J. Cardiol.*, 671, 674 (2009)).

The relative lack of success for AF patients arises largely from the inability of prior technologies and methods to accurately map and determine the source locations and mechanisms leading to AF in individual patients. AF is characterized by complex, variable self-perpetuating electrical activities in the heart. This presents a two-fold problem. First, the source locations and mechanisms leading to AF differ between patients. Second, the complex and variable nature of source locations and mechanisms leading to AF make them difficult to map and determine. Consequently, physicians are left with treating patients using generalized strategies that fail to account for the unique presentation of AF in individual patients. In terms of ablation, this often means that sources of AF are left untreated. Concurrently, healthy heart tissue is ablated, which can actually increase a patient's likelihood of developing arrhythmias.

SUMMARY

The present disclosure describes cardiac mapping techniques that find particular use in assessing fibrillation, and which also improve the ability to correctly identify local activation time from signals in any rhythm. The use of simultaneously obtained electrode data according to the invention enables one to determine relative positions of measurements made by multiple electrodes in the construction of a map of cardiac rhythm. Methods of the invention by which direction of activation is projected to the heart surface are unaffected by motion (e.g., cardiac or respiratory). This, then, allows the generation of a more precise cardiac map and avoids the impact that motion has on projections of non-simultaneously acquired electrode data onto the cardiac surface.

Methods and systems of the invention for cardiac mapping of a patient comprise positioning a two-dimensional electrode array at a location in a patient's heart, wherein the two-dimensional electrode array comprises a plurality of electrodes, which may be microelectrodes, distributed across the array at known locations and each electrode is separated by a known distance. At least one local activation signal and activation time is detected at each electrode of the array. For each group of electrodes of the array a conduction velocity (CV) vector is calculated based upon the activation time of each group of electrodes in the array.

For example, calculating a conduction velocity (CV) vector in the vicinity of any three adjacent electrodes of the array arranged non-linearly may be based upon the activation time of the first electrode, the activation time of a second electrode, and the activation time of a third or subsequent electrode. Calculating the aforementioned CV vector can further comprise determining the activation time of the local activation signal for the first electrode, the second electrode, and the third or subsequent electrode and obtaining the difference between the activation time of the first electrode and the second electrode, between the activation time of the first electrode and the second electrode, and the second electrode and the first electrode. Then, obtaining the respective distances between each of the first, second, and third electrodes, calculating a velocity vector between each of the first, second, and third electrode, and combining the velocity vectors.

After a CV vector is calculated for each group of electrodes in the two-dimensional array, an isochronal activation map may be compiled, which comprises the two-dimensional electrode array and the CV vector for each group of electrodes. The methods and systems of the disclosure can further comprise mapping the trajectory of a cardiac activation wave based on the CV vectors for adjacent electrodes of the two-dimensional electrode array.

Based upon the computed conduction velocity between any two closely spaced points on the map, the presence of a conduction block may be determined. In one embodiment, if a conduction block is present, the CV vector for each electrode of the array is recalculated. In another embodiment, conduction block may be determined prior to computing CV vectors, by computing the conduction velocity vector between every pair of adjacent electrodes, determining that the CV is at or above physiological limits, and excluding measurements which are outside of physiological limits. Detecting a conduction block may comprise determining that the difference between activation times between two or more electrodes is above a threshold indicative of direct propagation of the cardiac activation wave between the two or more adjacent electrodes.

Methods and systems of the invention may further comprise calculating the spatial context for each local activation signal of each electrode of the two-dimensional array. Calculating the spatial context may comprise constructing a directed graph connecting adjacent electrodes having closely-related activation times to identify clusters of spatio-temporally related activations. Then, a single contiguous cardiac activation wave for each cluster of spatio-temporally related activations can be determined.

A wave score may be calculated for each contiguous cardiac activation wave. The wave score for each cardiac activation wave is a function of an average activation score and the number of electrodes/activations that comprise the cardiac activation wave. For example, the wave score may be the product of average activation score and the number of electrodes/activations that comprise the cardiac activation wave. A contiguous cardiac activation wave with a wave score below a threshold may be discarded.

Systems and methods of the invention further provide that closely related activation times between a first electrode and one of a second electrode and one or more additional electrode may include computing a context weight for a given activation. The context weight may comprise determining the difference between the activation time of the first electrode relative to a distance-weighted average activation time of adjacent electrodes and the standard deviation of activation time of adjacent electrodes.

Methods and systems of the invention may comprise calculating the temporal context for each local activation signal of each electrode of the two-dimensional array. Calculating the temporal context may comprise detecting a plurality of local activation signals at one or more electrodes of the two-dimensional array and determining whether the activation times for each of the plurality of local activation signals for each of the one or more electrodes fall within a single refractory period.

Methods and systems of the invention may include calculating both the spatial context and temporal context for each local activation signal of each electrode of the two-dimensional array. Further, data may be collected over multiple waves and aggregated. This aggregated data can reveal substrate-mediated patterns of conduction. The invention is applicable to cardiac arrythmias generally including, but not limited to, ventricular fibrillation and atrial fibrillation.

DESCRIPTION

The present disclosure provides methods and systems for analyzing electrograms from groups of adjacent electrodes and creating wave maps, which may be a computational precursor to tissue substrate maps (e.g., wavelength maps). During AF, individual wave maps may be used to compute, inter alia, conduction velocities, detect functional block, detect focal breakthrough between endo- and epicardium, and to compute minimum cycle length (a correlate of local refractory period). By combining wave maps collected over an extended time period and over multiple locations, statistical methods may be applied to determine additional characteristics of tissue substrate.

Even with the best electrodes, it is often difficult to distinguish true local activations from spurious noise, injury currents, or far-field signals. Some functional metrics, such as minimum cycle length, are very sensitive to false positive activation detection. It is therefore critical to eliminate such signals with a high rate of accuracy. Applying electrograms within the context of their neighbors and applying physiological limits of conduction velocity one can increase detection accuracy.

For example, persistent AF is known to be correlated with substrate changes in cardiac tissue in the atria. By mapping substrate and characterizing inhomogeneity in tissue, an ablation strategy may be developed to identify optimal target sites to terminate persistent AF, while sparing tissue from excessive damage due to ablation.

Substrate abnormalities may manifest as variations in conduction velocity, minimum cycle length, and/or other measurable properties derived from intracardiac signals. Therefore, analysis of signals may be applied in order to deduce substrate characteristics. The approach provided by the present disclosure uses the acquisition of high spatial resolution signals from a small two-dimensional region of tissue, to create a local activation map for the purpose of deriving local tissue properties and then to create a three dimensional map of spatial gradients of tissue properties (rather than activation). This approach allows sequential mapping of fibrillation and therefore allows an arbitrarily high sample density, unconstrained by the number of electrodes deployed to the heart.

A novel catheter with an array of specialized electrodes is used to resolve electrograms at high spatial resolution, largely free of fractionation, where distinct activations are readily identifiable. By combining these electrodes, which may be micro-scale, into an array, temporal and spatial relationships of adjacent activations may be analyzed and used to create maps of distinct waves of activation. From these maps of fibrillation, the tissue properties that determine the type and distribution of arrhythmogenic drivers may be deduced.

Measuring Conduction Velocity (CV)

Figure 1:
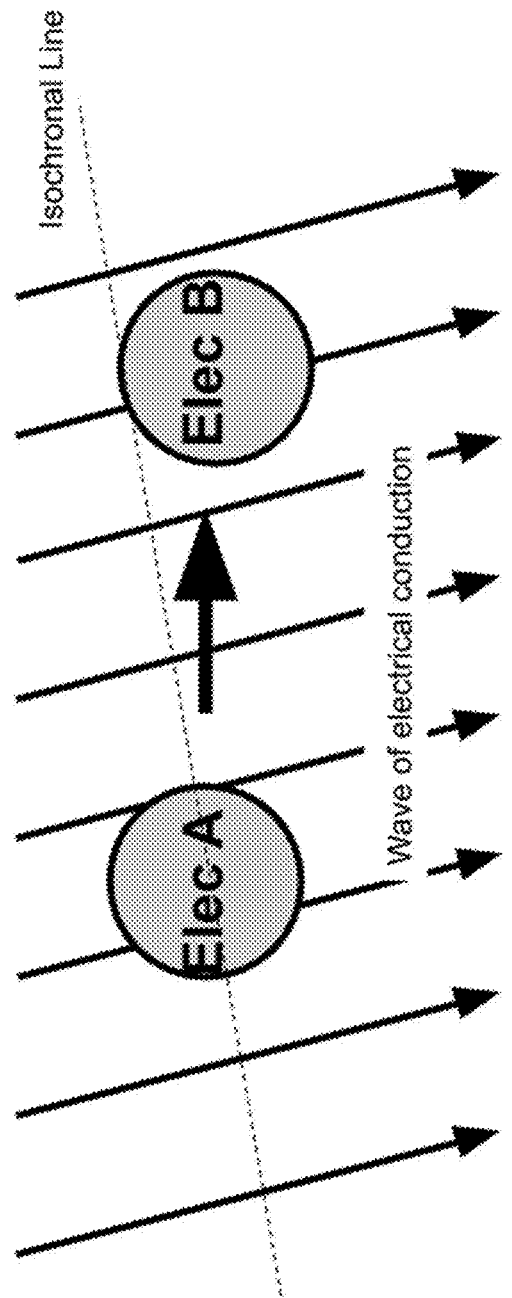
FIG. 1 shows a two-electrode arrangement for measuring a wave.

To accurately measure CV, it is preferred to use at least three electrodes arranged in a 2-dimensional layout. FIG. 1 illustrates the limitation of having only two electrodes. FIG. 1 shows a common two electrode arrangement used on prior methods and systems, such as with linear EP catheters, including those with a lasso configuration.

In FIG. 1, a wave of propagating signal is traveling along a downwards diagonal. Electrodes A and B measure respective timing. The wavefront will cross electrode A before B, and therefore A will have an earlier timing than B. A CV may be computed from this timing. However, this velocity merely represents just one component of a 2-dimensional gradient vector. Moreover, the velocity will have a much higher velocity value than the actual local CV.

Figure 2:
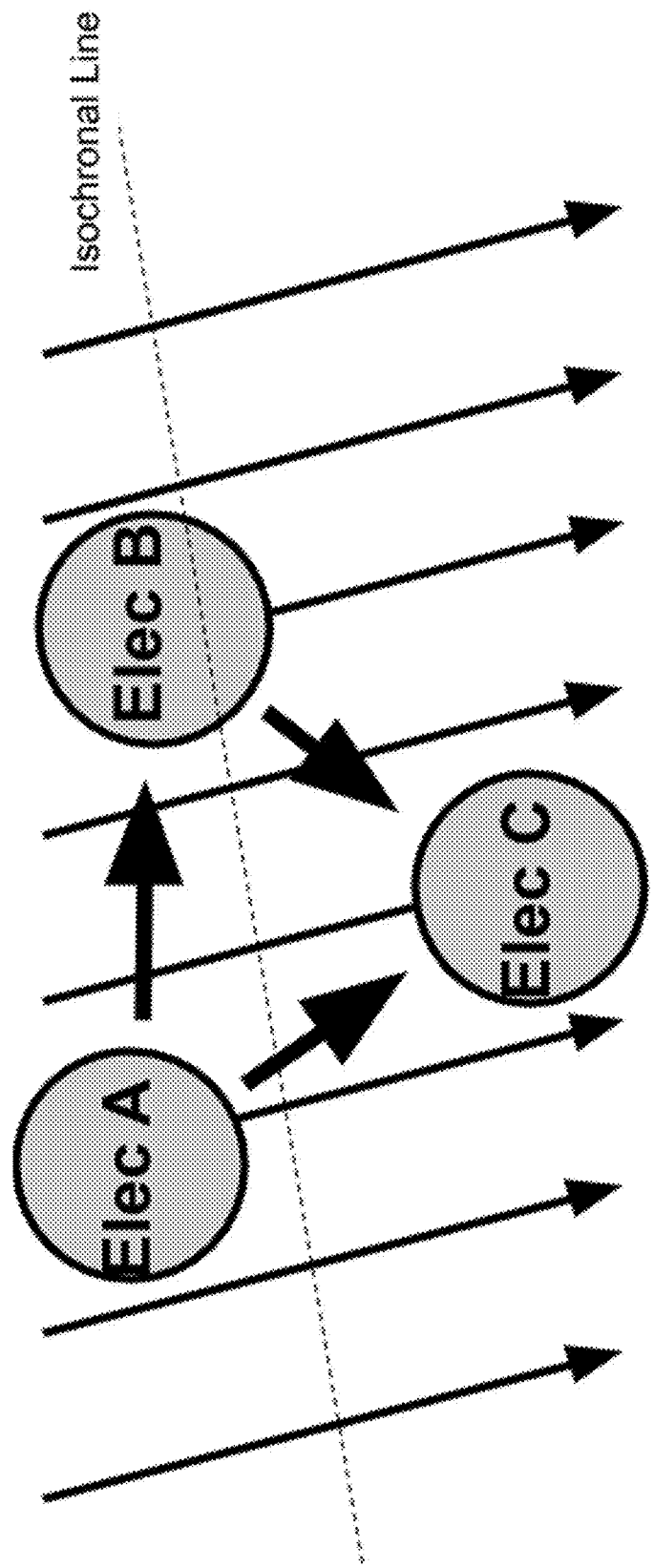
FIG. 2 shows a three-electrode arrangement for measuring a wave.

FIG. 2 shows the same wavefront, but in this case, a third electrode (C) is added. This is a type of electrode arrangement used in the methods and systems of the disclosure. Now, instead of a single measurement vector, the three-electrode arrangement provides three vectors. Critically, three vectors are sufficient to accurately compute a velocity vector along the true direction of the conducting wave.

Figure 3:
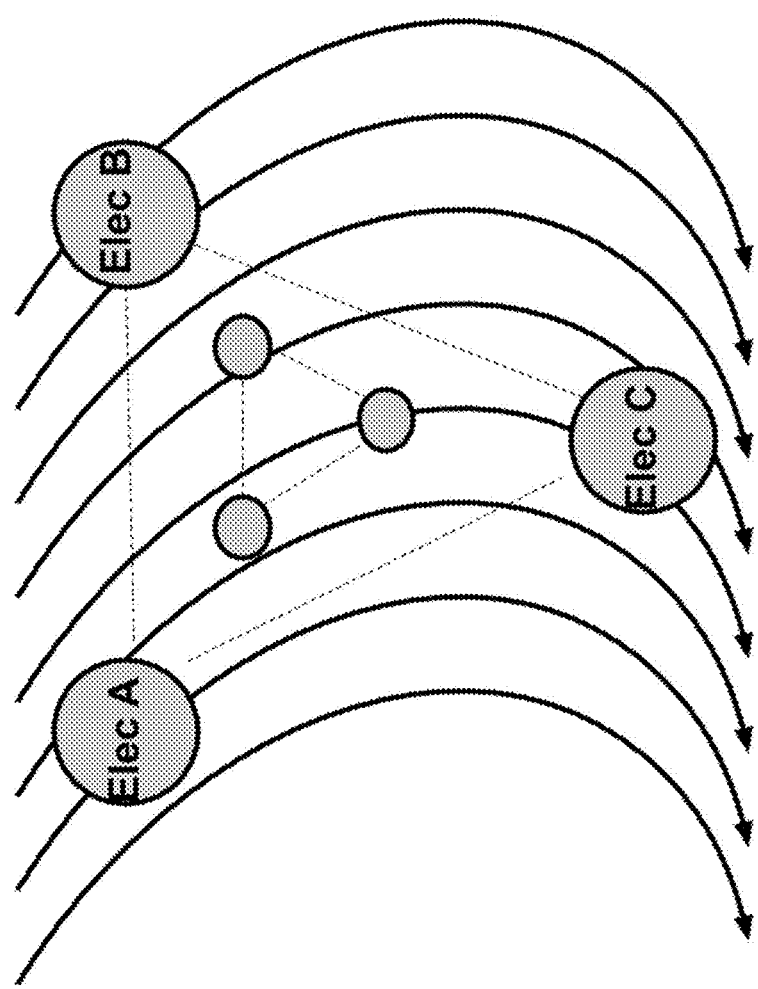
FIG. 3 shows two three-electrode arrangements using electrodes of various sizes to measure a wave.

Waves of electrical conduction are rarely linear, as illustrated above. For example, in practice, waves may curve (e.g. around regions of functional block). To accurately measure CV, it is important that electrodes are both small and tightly spaced. This can best approximate a linear wave. In FIG. 3, the three larger electrodes with larger spacing may yield an inaccurate CV based on the curvature of the wave. In contrast, the smaller electrodes in the middle are focused on a smaller part of the wave where the wavefront is relatively linear. Accuracy of measuring CV is also affected by the temporal accuracy of detected activations. Temporal accuracy is governed by two parameters. One parameter is the magnitude of the dV/dt slope of the detected activation. The magnitude of the slope increases inversely with the size of electrodes used for measuring activation, and is also proportional to contact distance between the electrodes and the cardiac surface. A sharper slope may yield a more accurate activation time. The second parameter is the rate at which signals are sampled by electronic analog-to-digital conversion. According to Nyquist sampling theorem, a higher sampling rate will be correlated with more accurate estimation of true local activation time.

Thus, using three small and tightly spaced electrodes, as in the methods and systems of the present disclosure, a velocity vector along the true direction of the conducting wave can be determined.

Measuring Functional Block

Once an accurate method of measuring CV is established, activation thresholds may be applied. These activation thresholds distinguish activations that are truly connected to one another, from those which are likely to be separated, for example, by a functional block.

Figure 4:
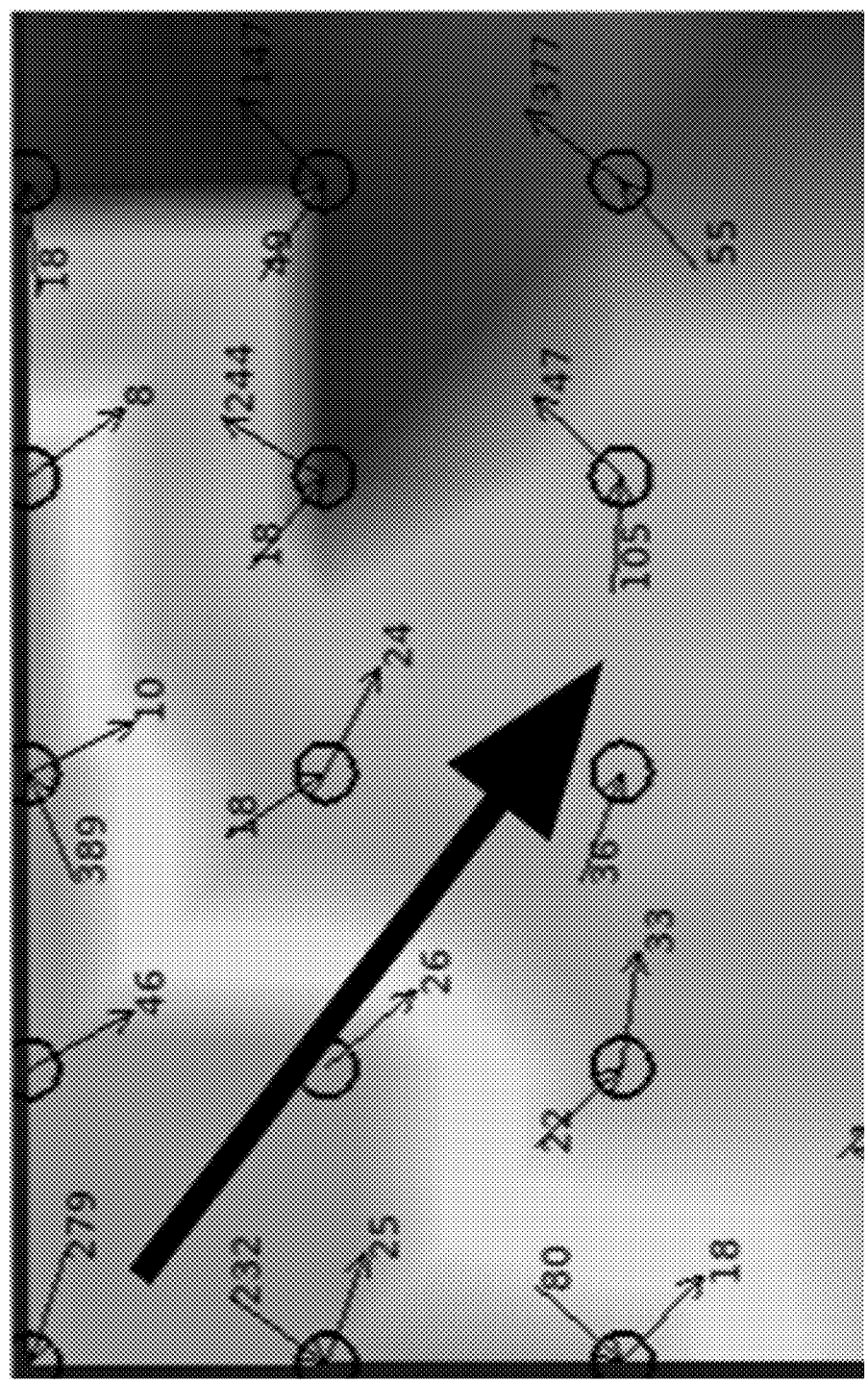
FIG. 4 shows an activation map.
Figure 5:
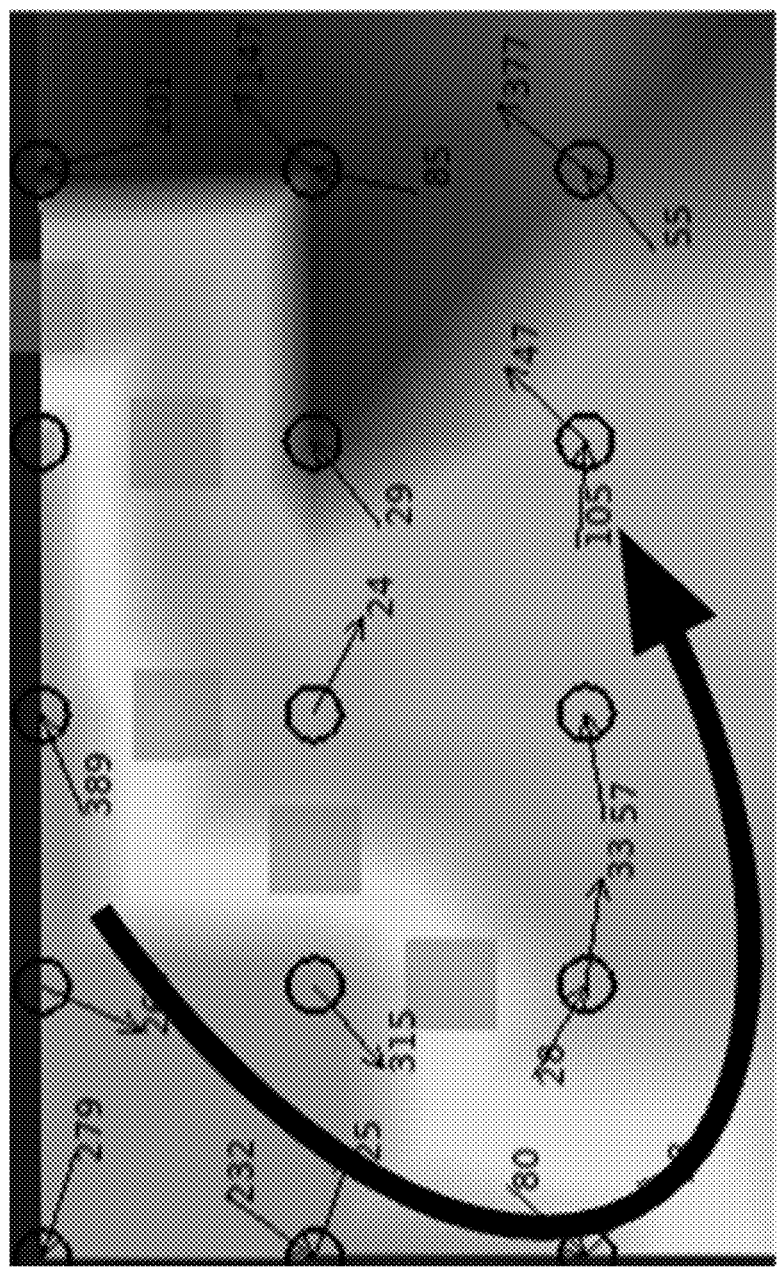
FIG. 5 shows an activation map with a conduction block.

FIGS. 4-5 provide a representative example of activation threshold application. FIG. 4 shows an isochronal activation map collected from an array of micro electrodes. Based on relative timings of activation, conduction appears to propagate from top-left to bottom-right of the image. In FIG. 4, circles indicate electrode locations. Arrows that end on circles indicate conduction towards electrode, while arrows that begin at circles indicate conduction away from the electrode. Numbers are conduction velocity shown in cm/sec. The large arrow indicates putative conduction direction.

FIG. 5 shows the benefits derived from applying activation thresholds. As shown in FIG. 5, activation thresholds provide a very different and more accurate indication of activation. As it turns out, the timing differences between some of the electrodes are too large for propagation to have been directly from one electrode to the other. The present methods and systems of the disclosure can recognize this inconsistency with physiological limits and tags certain positions along the map as manifesting conduction block, as indicated by the small grey squares. The systems and methods of the disclosure include algorithms to detect and map these inconsistencies. Consequently, conduction velocity is recomputed and the wave of activation appears to curve around the area of block. The large arrow in FIG. 5 shows the corrected putative conduction direction.

Assessing Focal Breakthrough

In some cases, computation of conduction vector shows conduction emanating from a single point on the map. This is commonly called focal activation and may be indicative of an isolated driver or a break-through from one heart surface to the other (e.g. endo- to epicardial layers). Areas of common breakthrough may be of clinical interest as potential targets for ablation.

Figure 6:
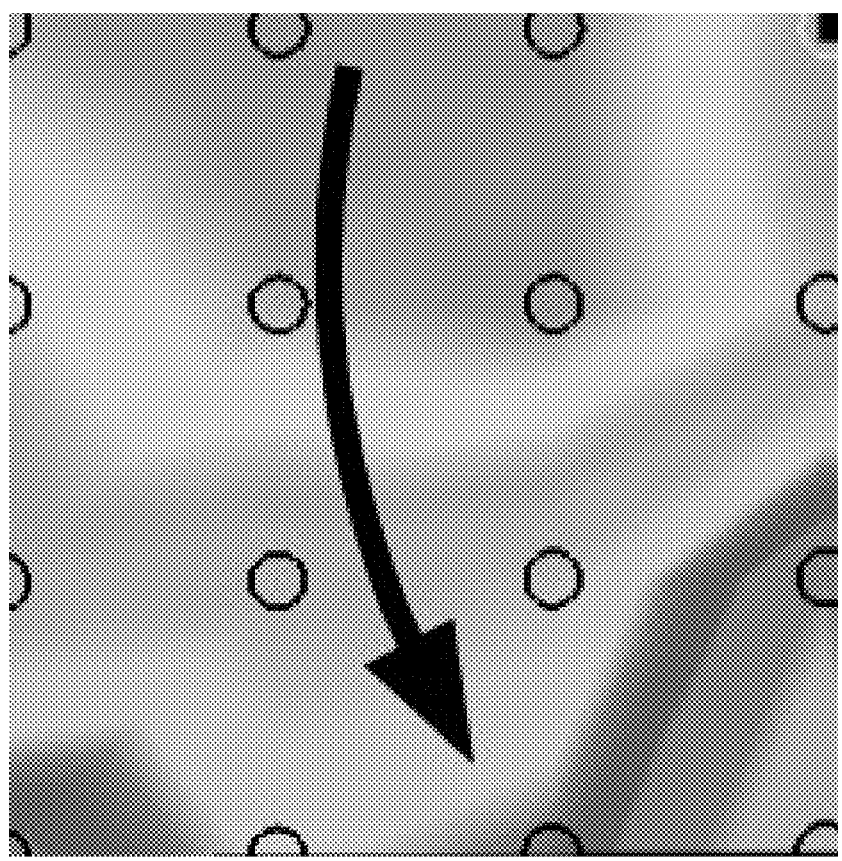
FIG. 6 shows an activation map of a 4×4 electrode array.
Figure 7:
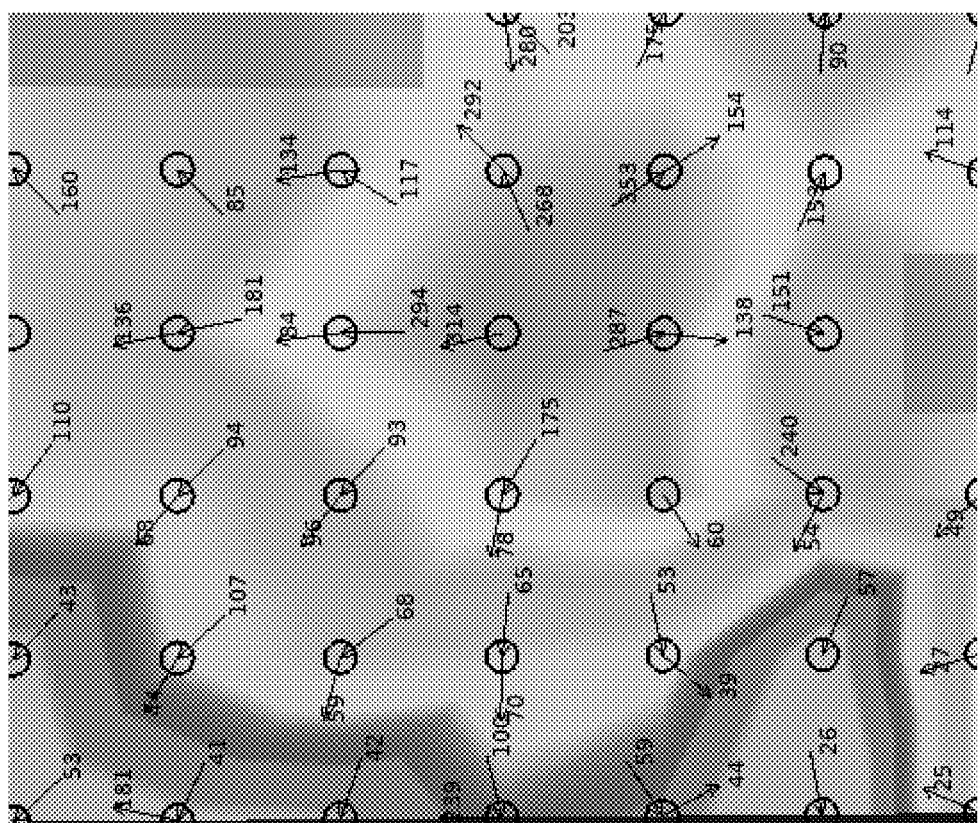
FIG. 7 shows an activation map using a large electrode array.

A large contiguous 2D array is essential for accurate detection of focal sites in fibrillation. FIG. 6 shows a 4×4 subset of array electrodes showing a conduction wave which appears to be traveling from right to left, as shown by the large arrow. In contrast, FIG. 7 shows the same data when viewed from all array electrodes. When viewing the full array of electrodes the wave in question is clearly focal.

Spatial Context

The examples of detecting functional block and focal breakthroughs illustrate some uses of spatial context. In these examples, information from multiple adjacent electrodes allows the trajectory of a cardiac activation wave to be mapped. This would be impossible possible using data from a single electrode or linear array, as is done in prior methods.

By using a sufficiently large number electrodes and maintaining regular consistent spacing between electrodes, spatial context allows us to extract other types of information. There are several ways in which spatial context may be computed and applied. These are described below.

Assignment of Activation Clusters into Waves

Figure 8:
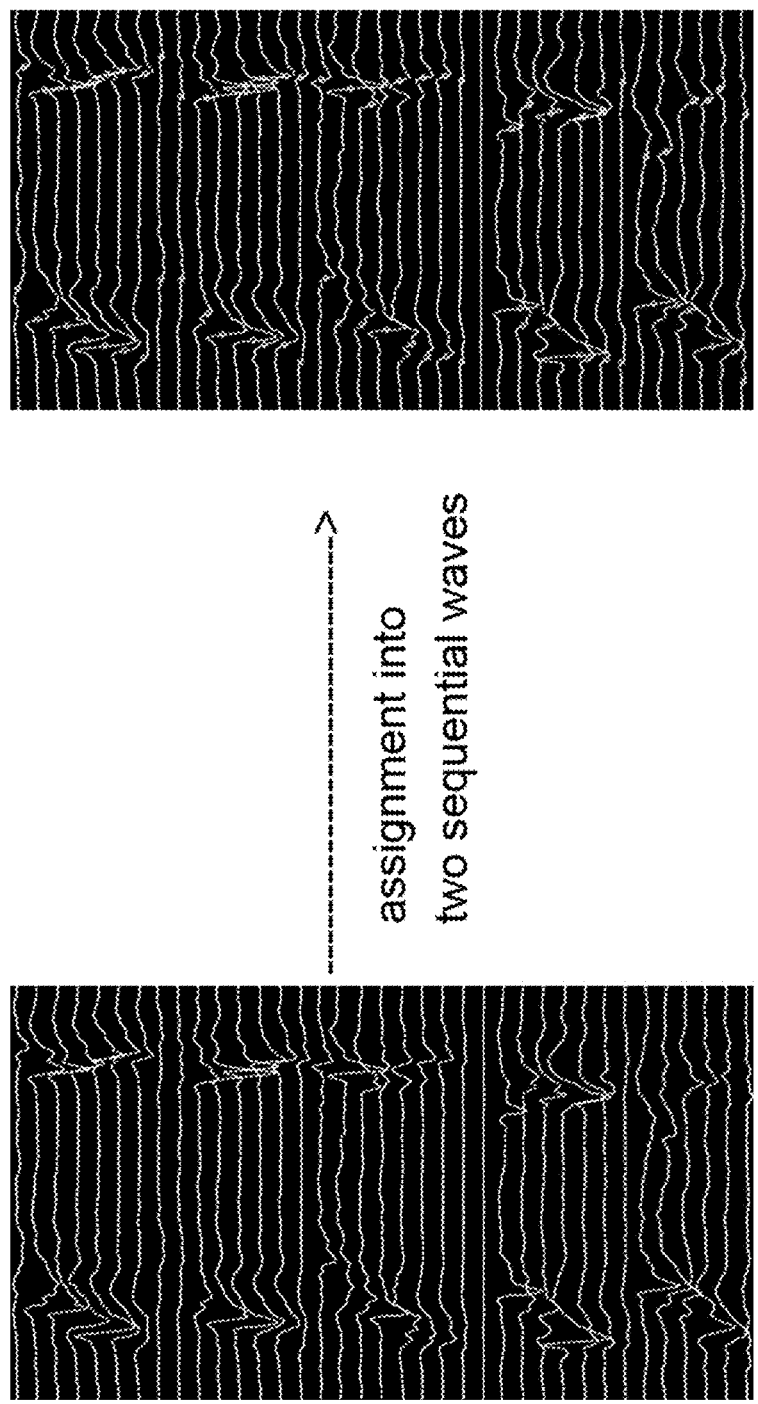
FIG. 8 shows electrograms revealing two contiguous waves.

The first step in utilizing spatial context is to identify clusters of spatio-temporally related activations. This can be done by constructing a directed graph connecting neighbor electrodes with closely related timing. By stepping through all electrodes, a single contiguous wave may be constructed. FIG. 8 shows how this approach separates a set of electrograms into two distinct waves of activation.

In FIG. 8, there are two completely distinct waves. In some cases, waves may overlap within their respective refractory periods as in the example below. Each electrode has a single activation, but the software groups them into two separate waves based on timing and spatial relationship. In FIG. 8 electrograms without (left) and with (right) color coded local activation time markers indicate the presence of the two separate waves (green dots and blue dots)

Figure 9:
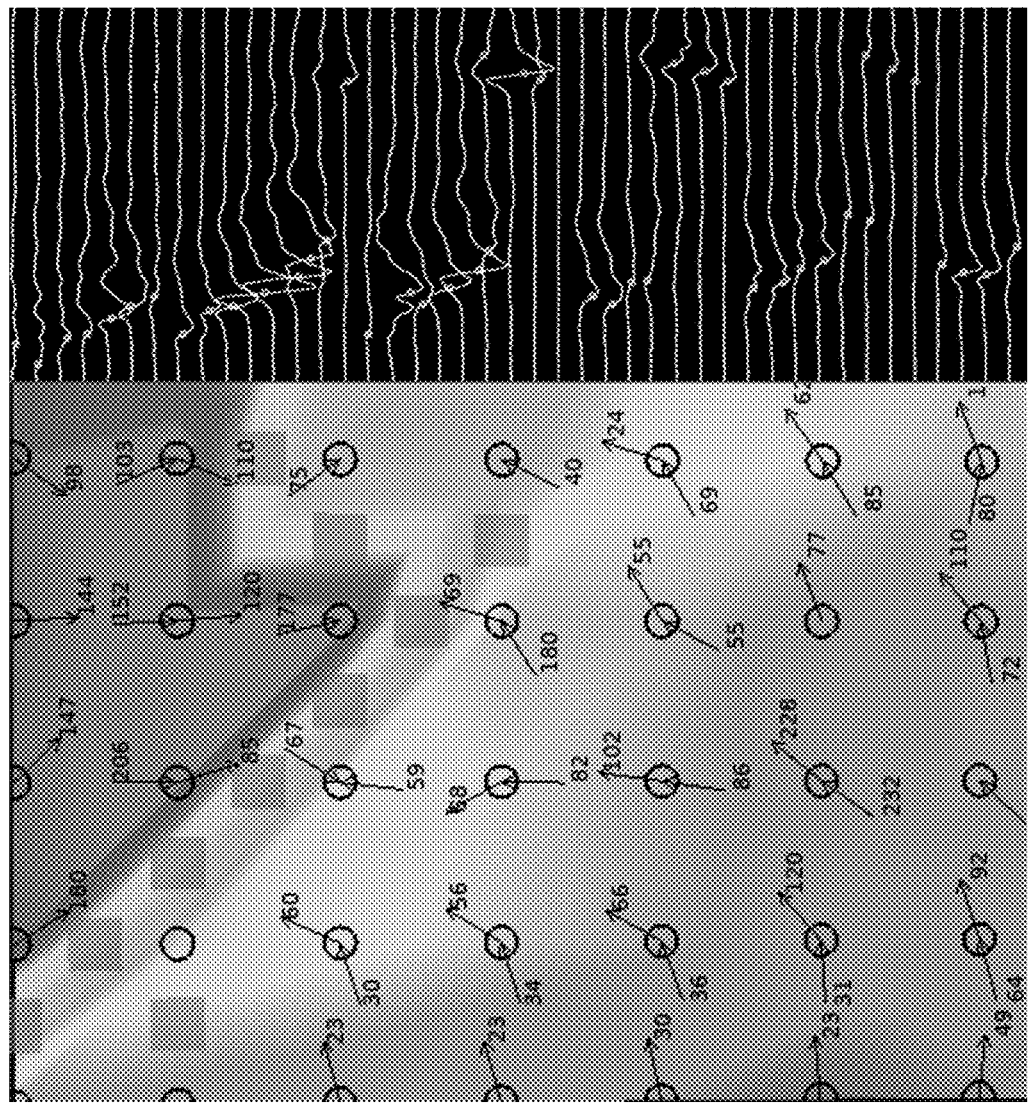
FIG. 9 shows an activation map and corresponding electrograms.

FIG. 9 depicts an activation map (left), in which the two distinct waves are separated by grey squares. The right panel of FIG. 9 shows the electrograms.

The accuracy of timing-based sorting of local activation times into waves can be assessed by examination of conduction vectors. For example, activation towards a putative line of block supports the presence of conduction block, while propagation away from the "far side" of a putative line of block suggests slow conduction rather than conduction block. This can be used to iteratively update the conduction velocity threshold used by the algorithm to identify block.

Figure 10:
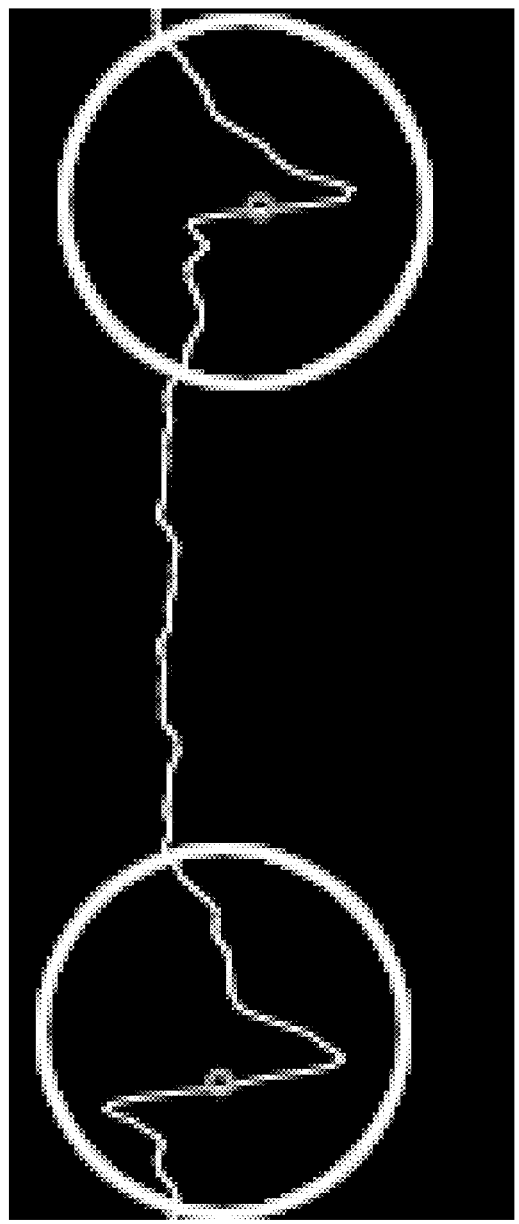
FIG. 10 shows an electrogram of an electrode showing two activations.

Distinguishing Between "Candidate" Local Activation Times Using Local Context: Wave Scoring FIG. 10 shows two adjacent activations from a single electrode. Both appear to be sharp deflections, which may be indicative of a physiological local activation. In the absence of context information, the software may mark both deflections as local activations.

Figure 11:
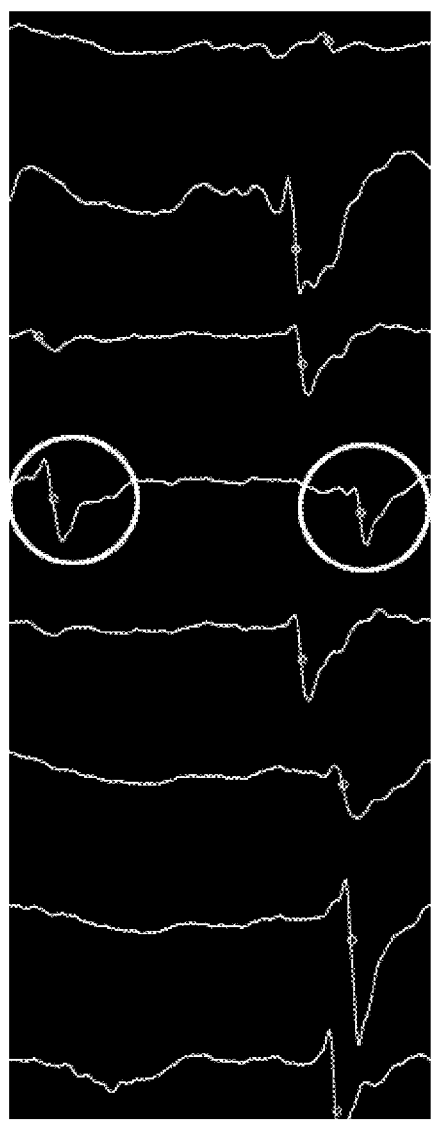
FIG. 11 shows an electrogram of an electrode showing two activations in context with electrograms of neighboring electrodes.

FIG. 11 shows the same electrode in the context of its neighboring electrograms. The methods and systems of the disclosure can identify two distinct waves. This may include the use of software and/or algorithms. By visual inspection, it is clear that the right-most electrogram is supported by data from its neighbors as being part of a discrete strong wave, whereas the left-most appears to be some kind of anomaly.

The methods and systems of the disclosure can identify two separate waves, but the one on the right is visibly more supported by a plurality of electrodes with matching deflections. A wave score is computed for each wave. Any wave with a score below a prescribed threshold is discarded. The wave score may be a function of two inputs. The first input is an average activation score, which itself may be a function of dV/dt and/or amplitude of the deflection. The average activation score may be the RMS of all individual deflections. The second input is the number of electrodes/activations that comprise a single wave. For example, the wave score may be the product of average activation score and number of activations.

Wave scoring may be used to eliminate spurious activations which may be a result of noise or far-field signals or injury current. This allows effective "filtering out" of spurious signals without altering the data (e.g. without frequency-based filtering).

Context-Weighted Score for Individual Electrograms

In some electrograms, where two or more activation timings are equally likely candidates, context may be used to select the activation which fits more accurately with its neighbors.

Figure 12:
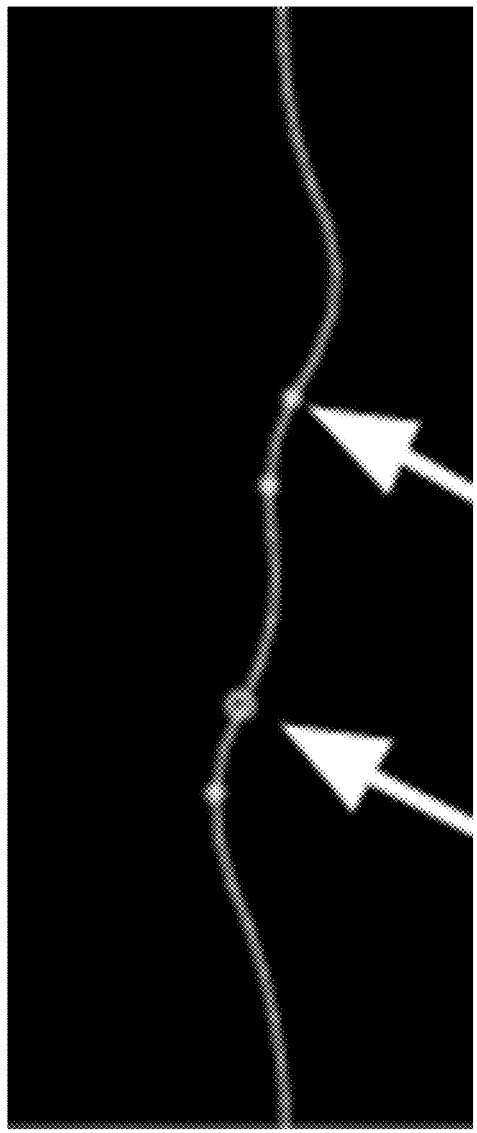
FIG. 12 shows an electrogram depicting a double activation.

The electrogram in FIG. 12 depicts a double activation. Both downward deflections, marked with large arrows, are approximately equal in slope and amplitude.

Figure 13:
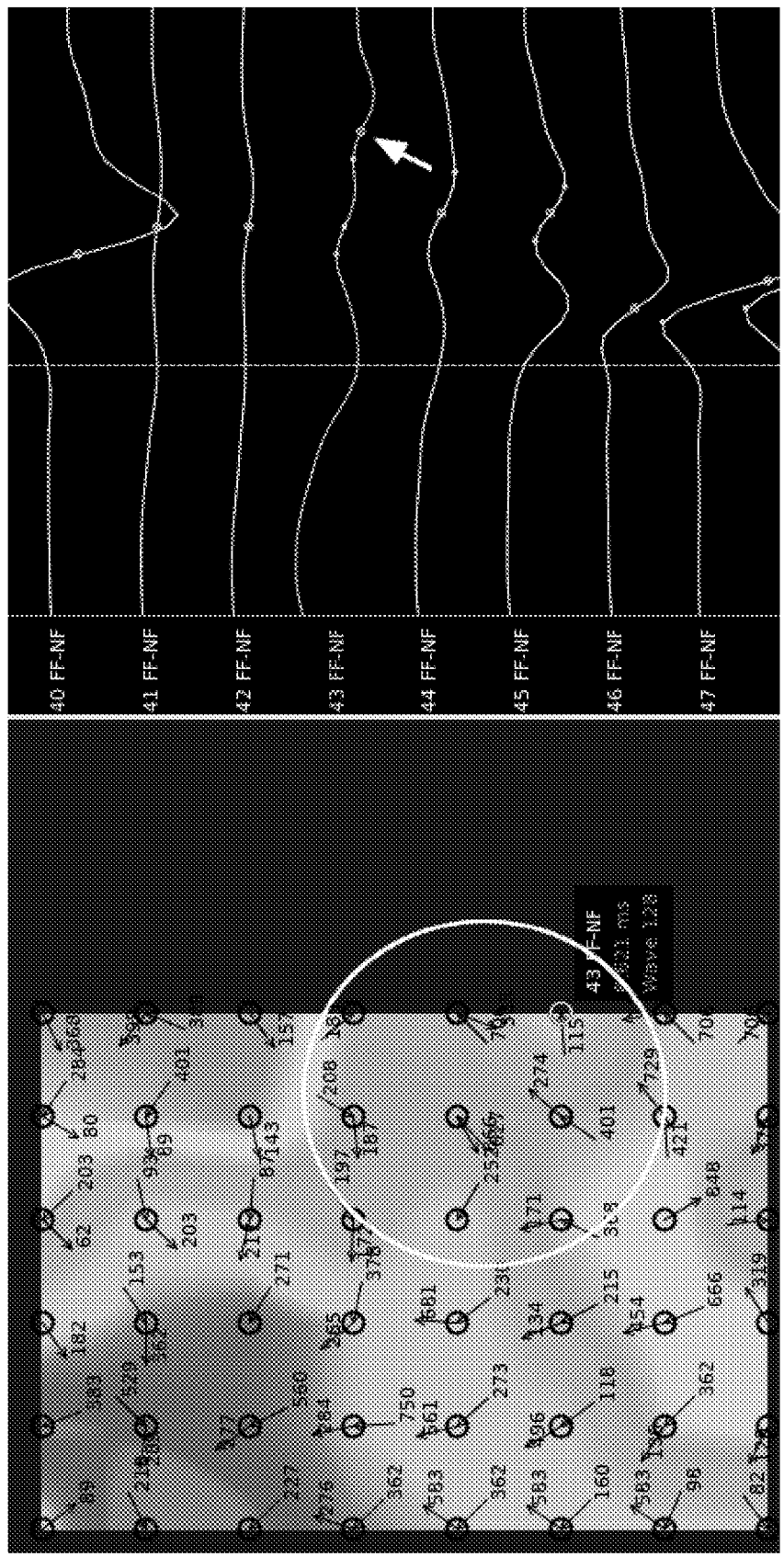
FIG. 13 shows an activation map and corresponding electrogram.

The image in FIG. 13 shows the original selected deflection, without consideration for local context.

Figure 14:
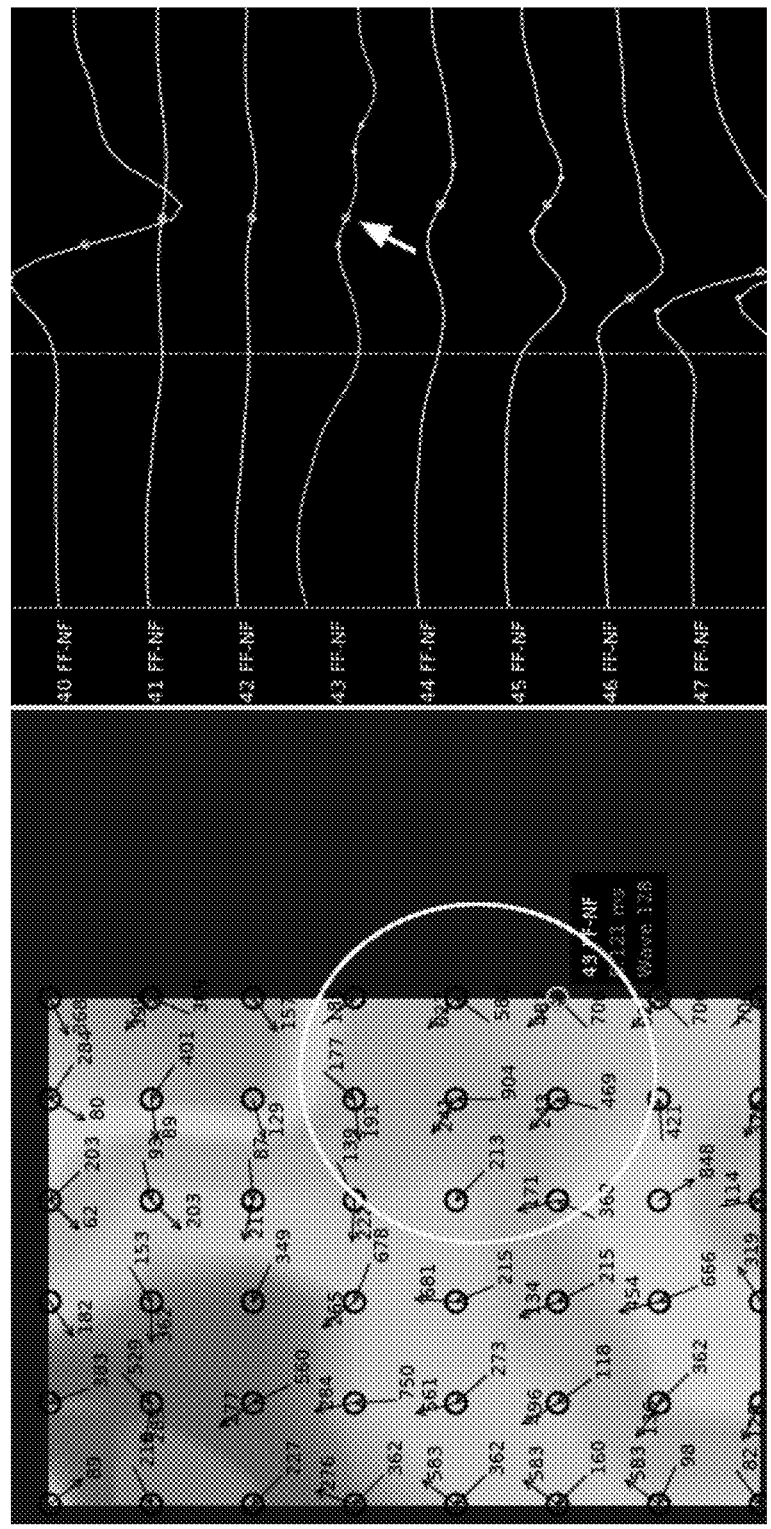
FIG. 14 shows an activation map and corresponding electrogram after applying context correction.

In contrast, the image in FIG. 14 shows how context correction changes and improves the accuracy of the selected activation. Consequently, the activation map also displays a more consistent pattern of activation in the affected region.

A context weight for a given activation may be computed as follows:

$\Delta t$=time difference relative to distance-weighted average activation time of neighbors;

$\sigma$=standard deviation of activation time of neighbors; and context score is $1/(1+\Delta t/\sigma)$ Assignment of local activation times into discrete waves/portions of waves, increases the accuracy of conduction velocity calculations by eliminating errors introduced by incorrectly calculating conduction velocity between two electrodes in the absence of actual direct propagation between them.

Temporal Context

Whereas spatial context examines an electrogram for adherence to physiological CV constraints within the context of its spatially adjacent neighbors, temporal context tests refractory period constraints with respect to the temporally nearest neighboring deflections for an electrogram.

Figure 15:
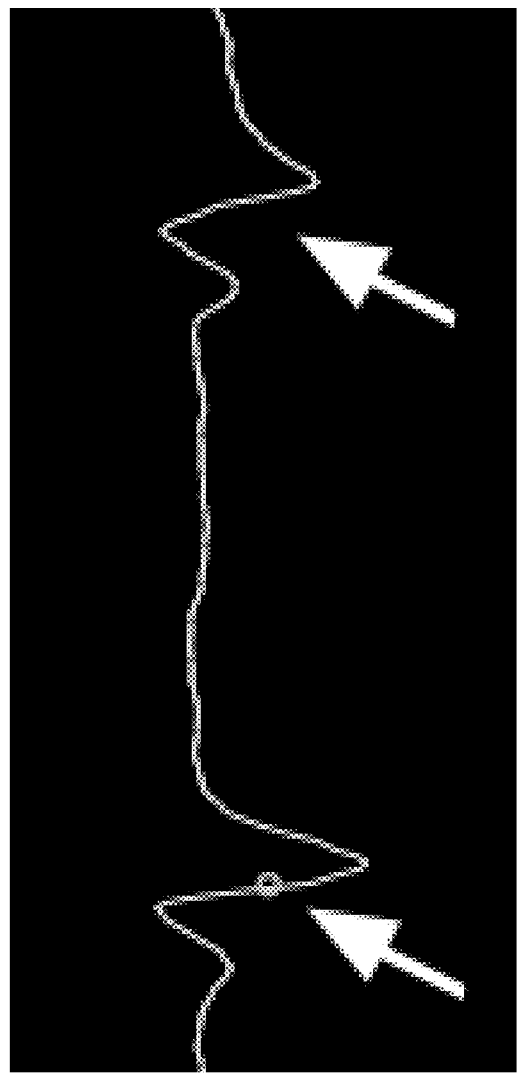
FIG. 15 shows an electrogram of a single electrode with two activations within a single refractory period.

The electrogram in FIG. 15 shows two activations, indicated by the two arrows, which are 60 ms apart. Physiologically, it is unlikely that a cardiac cell could be activated twice in such a short time interval due to tissue refractoriness. Temporal context suggests that these activations may be coming from different groups of muscle cells.

Figure 16:
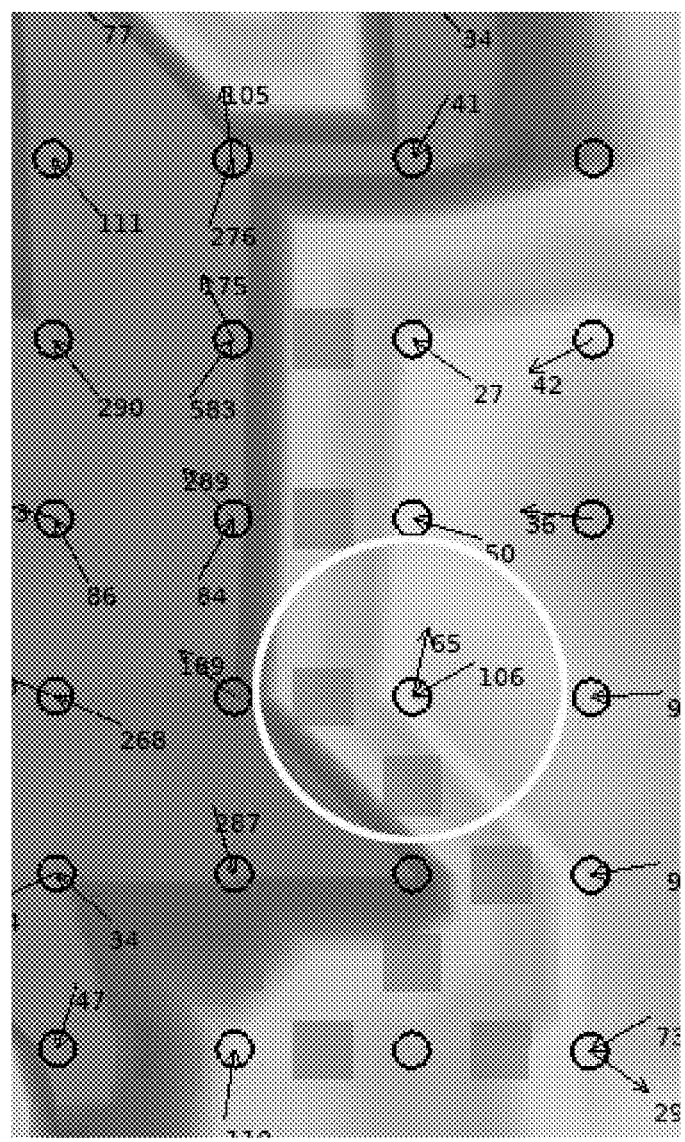
FIG. 16 shows an activation map.

In this example, closer inspection of the map, shown in FIG. 16, reveals that this electrogram sits at the boundary of two separate waves, which lends support to the temporally derived hypothesis that the deflections are coming from distinct groups of muscle cells.

Using this information, which combines a temporally derived hypothesis with spatial context, it can be determined the timing between these two deflections should not be considered for computing minimum cycle length at this location on the cardiac surface.

Statistical Methods

Data collected over multiple waves may be aggregated to reveal substrate-mediated patterns of conduction. Such patterns may include, but are not limited to: areas of frequent focal breakthrough; areas of frequent (or infrequent) functional block; and elimination of false positive minimum cycle length through comparison with all cycle lengths acquired at a particular location.

Motion

The methods described herein are largely unaffected by cardiac or respiratory motion due to the density and spacing of electrodes on the array. In conventional cardiac mapping systems, very few electrodes are in contact with the cardiac surface. Consequently, to assemble high resolution maps requires stitching together data acquired from different heart beats. This stitching process is highly susceptible to variations in catheter location due to motion of the heart or the diaphragm or to voluntary patient movement. With a high-density 2-dimensional array, it is possible to collect a sufficient quantity of data from a single activation wave within a narrow time window (of approximately 100 ms or less), so as to compute all aforementioned parameters, including CV, which may be very sensitive to location uncertainty. Unlike conventional mapping systems, we may refer to two levels of computation: a "micro" level at the level of a single array location, and a "macro" level referring to an entire chamber.

A complete macro substrate map of an entire chamber would entail stitching together micro single-location maps. At the macro level, motion artifact would then be more of a factor. However, stitching of macro substrate maps and correlation with ablation target sites does not require such a high degree of precision as computation of CV or accurate assessment of functional block at the micro level. Therefore, conventional methods of motion management may be used for macro computation, including respiratory gating, extracorporeal location reference sensors, and low-pass filtering of cardiac motion.

Catheters

Figure 17A:
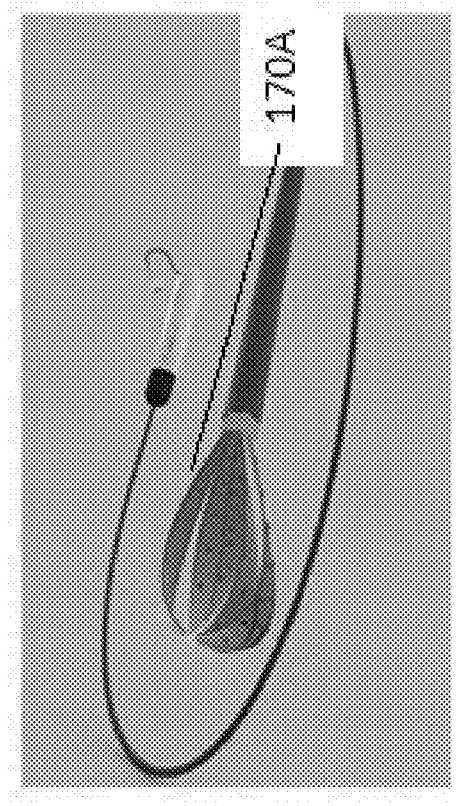
FIGS. 17A-17B show exemplary catheters.
Figure 17B:
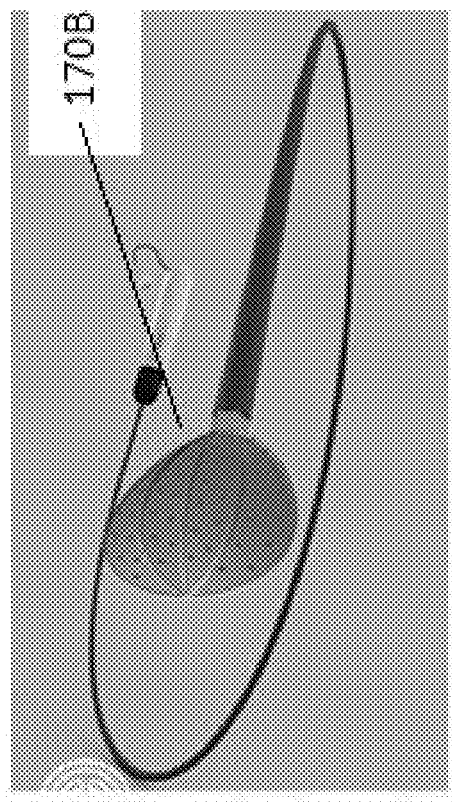

The systems and methods of the disclosure may incorporate or use one or more catheters to which the disclosed electrode arrays are attached. FIGS. 17A-17B show exemplary electrodes. Each catheter has a distal end (170A and 170B) on which the electrode array is disposed. The distal ends of these catheters are inserted into a patient's heart, and the electrode arrays are deployed.

Catheters of the present disclosure may also be used in conjunction with surgical devices for accessing a patient's heart, i.e. sheaths with valves, and one or more guidewires for positioning catheters.

Catheters of the disclosure may also be used in conjunction with an imaging subsystem. This can allow, for example, viewing tissue and/or the catheter while deployed inside a patient.

Catheters may also be deployed in conjunction with electrode localization technologies, including radio frequency-based localization, triangulation based localization, and/or impedance based localization.

Electrodes

The present disclosure provides systems and methods using electrode arrays that can be positioned within a patient's heart. An electrode is an electrical conductor. Electrodes of the present disclosure include electrodes, which may be solid conductors, such as needles or discs.

Electrodes of the present disclosure may be configured as unipolar electrodes. In a pair of unipolar electrodes, a first electrode, the "index electrode", is proximal to tissue such that it records a signal. A second electrode, the "indifferent electrode" is positioned away from tissue such that it does not record a signal.

Electrodes of the present disclosure may be configured as contact bipolar electrodes. In a pair of contact bipolar electrodes, both electrodes are proximal to tissue such that each records a signal.

Electrodes of the present disclosure may be configured as orthogonal close unipolar (OCU) electrodes. In a pair of OCU electrodes, the index electrode and indifferent electrodes are in a stacked arrangement and positioned orthogonal to a tissue. The index electrode and indifferent electrode are separated by an inter-electrode space that is likewise orthogonal to the tissue. The inter-electrode space is preferably between approximately 0.01 mm and 1 mm.

OCU electrodes have been shown to be particularly effective in the context of mapping fibrillation. OCU electrodes retain the ability of contact bipolar electrodes to exclude far field electrical activity endemic to unipolar configurations. Further, OCU electrodes retain the directional independence and small footprint of unipolar configurations, which are lacking in contact bipolar configurations.

Figure 18:
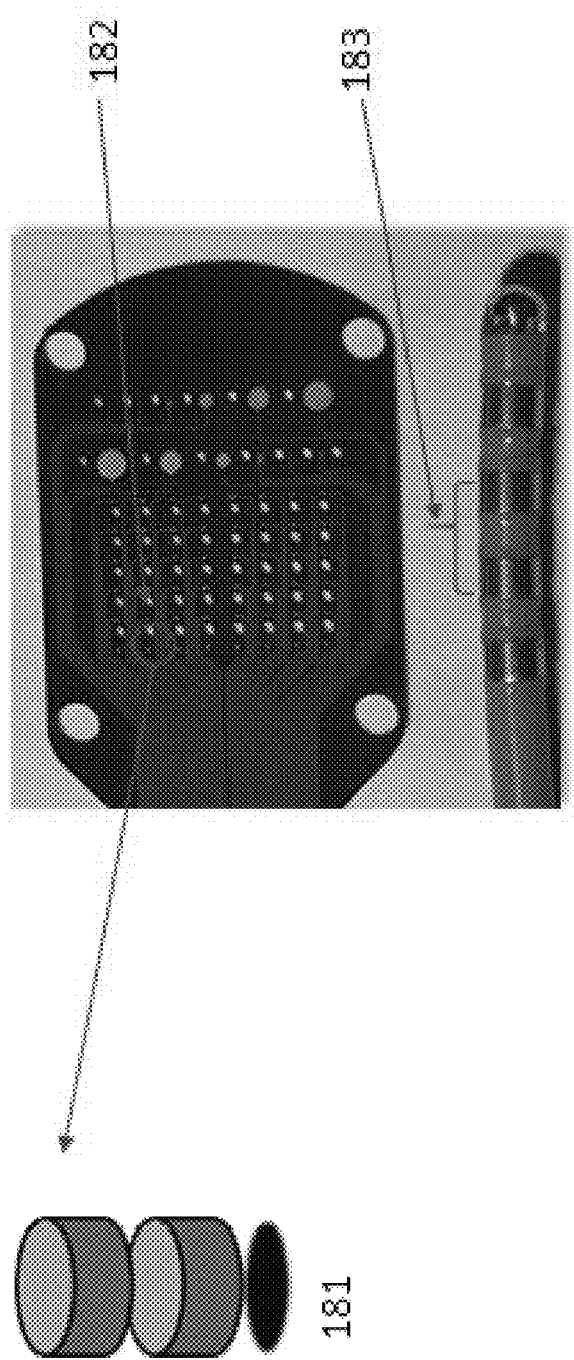
FIG. 18 shows OCU electrodes, an array of OCU electrodes, and a comparison with a prior six electrode catheter.

FIG. 18 shows an expanded view of a pair of OCU electrodes (181) and their placement on an array (182) of the present disclosure. Each OCU electrode pair of the array is approximately 100 μm in diameter, where the sensing surface area of the OCU electrode pair is nearly 800× smaller than the electrodes of the six electrode catheter (183), which is representative of prior technologies.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

What is claimed is:

1. A method for cardiac mapping of a patient comprising:
positioning a two-dimensional electrode array at a location in a patient's heart, wherein the two-dimensional electrode array comprises a plurality of electrodes arranged in a nonlinear configuration distributed across the array at known locations and each electrode is separated by a known distance;
simultaneously detecting at least one local activation signal and activation time at each electrode of the array; and
calculating a conduction velocity (CV) vector for a first electrode of the array using the activation time of the first electrode, the activation time of a second electrode, and the activation time of at least a third electrode to construct a map of cardiac electrical activity, and further determining a single point on the map from which the conduction emanates.

2. The method of claim 1, wherein calculating further comprises:
determining the activation time of the local activation signal for the first electrode, the second electrode, and the third electrode;
obtaining the difference between the activation time of the first electrode and the second electrode, between the activation time of the second electrode and the third electrode, and the first electrode and the third electrode;
obtaining the respective distances between each of the first, second, and third electrodes;
calculating a velocity vector between each of the first, second, and third electrode; and
combining the velocity vectors.

3. The method of claim 1, wherein a CV vector is determined with respect to a group of electrodes of the array using the activation time of a first electrode and the activation times of at least two adjacent electrodes.

4. The method of claim 3, further comprising compiling an isochronal activation map comprising the two-dimensional electrode array and the CV vector for each group of electrodes.

5. The method of claim 4, further comprising calculating the temporal context for each local activation signal of each electrode of the two-dimensional array.

6. The method of claim 5, wherein calculating the temporal context comprises detecting a plurality of local activation signals at one or more electrodes of the two-dimensional array and determining whether the activation times for each of the plurality of local activation signals for each of the one or more electrodes fall within a single refractory period.

7. The method of claim 4, further comprising mapping the trajectory of a cardiac activation wave based on the CV vectors for adjacent electrodes of the two-dimensional electrode array.

8. The method of claim 7, further comprising detecting a conduction block and calculating the CV vector for each electrode of the array to exclude the vector associated with conduction block.

9. The method of claim 8, wherein the step of detecting a conduction block comprises determining that the activation times between two or more adjacent electrodes are below a threshold indicative of direct propagation of the cardiac activation wave between the two or more adjacent electrodes.

10. The method of claim 9, wherein said threshold is adjusted based on a direction of a propagation vector with respect to a putative site of conduction block.

11. The method of claim 4, further comprising calculating the spatial context for each local activation signal of each electrode of the two-dimensional array.

12. The method of claim 11, wherein calculating the spatial context comprises constructing a directed graph connecting adjacent electrodes having closely related activation times to identify clusters of spatio-temporally related activations.

13. The method of claim 12, further comprising determining a single contiguous cardiac activation wave for each cluster of spatio-temporally related activations.

14. The method of claim 13, further comprising calculating a wave score for each contiguous cardiac activation wave, wherein the wave score for each cardiac activation wave is a function of an average activation score and the number of electrodes/activations that comprise the cardiac activation wave.

15. The method of claim 14, wherein the wave score is the product of average activation score and the number of electrodes/activations that comprise the cardiac activation wave.

16. The method of claim 14, wherein a contiguous cardiac activation wave with a wave score below a threshold is discarded.

17. The method of claim 12, wherein determining closely related activation times between a first electrode and one of a second electrode and third electrode comprises computing a context weight for a given activation.

18. The method of claim 15, wherein the context weight comprises determining the difference between the activation time of the first electrode relative to a distance-weighted average activation time of adjacent electrodes and the standard deviation of activation time of adjacent electrodes.

19. The method of claim 1, further comprising calculating the spatial context and temporal context for each local activation signal of each electrode of the two-dimensional array.

20. The method of claim 19, wherein data is collected over multiple waves and aggregated.

21. The method of claim 20, wherein the aggregated data reveals substrate-mediated patterns of conduction.

22. The method of claim 1, wherein the single point on the map from which conduction emanates is indicative of an isolated driver or a breakthrough from endocardial to epicardial layer.

* * * * *